United States Patent
Agassi et al.

(10) Patent No.: US 11,875,794 B2
(45) Date of Patent: Jan. 16, 2024

(54) SEMANTICALLY AUGMENTED CLINICAL SPEECH PROCESSING

(71) Applicant: CERNER INNOVATION, INC., North Kansas City, MO (US)

(72) Inventors: Emin Agassi, Blue Bell, PA (US); Jodi Kodish-Wachs, Albuquerque, NM (US)

(73) Assignee: Cerner Innovation, Inc., North Kansas City, MO (US)

(*) Notice: Subject to any disclaimer, the term of this patent is extended or adjusted under 35 U.S.C. 154(b) by 0 days.

(21) Appl. No.: 17/810,713

(22) Filed: Jul. 5, 2022

(65) Prior Publication Data

US 2022/0351728 A1 Nov. 3, 2022

Related U.S. Application Data

(63) Continuation of application No. 16/720,628, filed on Dec. 19, 2019, now Pat. No. 11,410,650.

(60) Provisional application No. 62/784,910, filed on Dec. 26, 2018.

(51) Int. Cl.
| | |
|---|---|
| *G10L 15/00* | (2013.01) |
| *G10L 15/22* | (2006.01) |
| *G16H 10/60* | (2018.01) |
| *G10L 15/18* | (2013.01) |
| *G06V 40/20* | (2022.01) |
| *G06V 40/16* | (2022.01) |

(52) U.S. Cl.
CPC .......... *G10L 15/22* (2013.01); *G10L 15/1815* (2013.01); *G10L 15/1822* (2013.01); *G16H 10/60* (2018.01); *G06V 40/172* (2022.01); *G06V 40/25* (2022.01); *G10L 2015/223* (2013.01)

(58) Field of Classification Search
CPC ......... G16H 10/60; G16H 15/00; G10L 15/26
See application file for complete search history.

(56) References Cited

U.S. PATENT DOCUMENTS

| | | |
|---|---|---|
| 7,379,946 B2 | 5/2008 | Carus et al. |
| 7,617,078 B2 | 11/2009 | Rao et al. |
| 7,630,947 B2 | 12/2009 | Pandya et al. |
| 7,725,330 B2 | 5/2010 | Rao et al. |
| 7,840,511 B2 | 11/2010 | Rosales et al. |
| 7,881,957 B1 | 2/2011 | Cohen et al. |
| 7,885,811 B2 | 2/2011 | Zimmerman et al. |
| 8,170,897 B1 | 5/2012 | Cohen et al. |
| 8,185,553 B2 | 5/2012 | Carus et al. |
| 8,209,183 B1 | 6/2012 | Patel et al. |
| 8,214,224 B2 | 7/2012 | Rao et al. |
| 8,214,225 B2 | 7/2012 | Rao et al. |
| 8,255,258 B1 | 8/2012 | Cohen et al. |

(Continued)

OTHER PUBLICATIONS

Chiu et al., "Speech Recognition for Medical Conversations", Available Online at: <arXiv preprint arXiv:1711.07274>, Nov. 20, 2017, 5 pages.

*Primary Examiner* — Daniel Abebe
(74) *Attorney, Agent, or Firm* — Mughal Gaudry & Franklin PC

(57) ABSTRACT

Methods and systems for processing of voice input to identify intents and mapped standard terminologies are provided. Using natural language processing, an intent of a voice input is identified. The intent is utilized to identify a standard terminology that maps to the intent. The standard terminology is utilized to identify information relevant to the standard terminology in a patient's electronic health record.

20 Claims, 6 Drawing Sheets

(56) References Cited

U.S. PATENT DOCUMENTS

| | | |
|---|---|---|
| 8,374,865 B1 | 2/2013 | Biadsy et al. |
| 8,428,940 B2 | 4/2013 | Kristjansson et al. |
| 8,498,892 B1 | 7/2013 | Cohen et al. |
| 8,510,340 B2 | 8/2013 | Carus et al. |
| 8,612,211 B1 | 12/2013 | Shires et al. |
| 8,694,335 B2 | 4/2014 | Yegnanarayanan |
| 8,700,395 B2 | 4/2014 | Zimmerman et al. |
| 8,738,403 B2 | 5/2014 | Flanagan et al. |
| 8,756,079 B2 | 6/2014 | Yegnanarayanan |
| 8,768,723 B2 | 7/2014 | Montyne et al. |
| 8,782,088 B2 | 7/2014 | Carus et al. |
| 8,788,289 B2 | 7/2014 | Flanagan et al. |
| 8,799,021 B2 | 8/2014 | Flanagan et al. |
| 8,831,957 B2 | 9/2014 | Taubman et al. |
| 8,878,773 B1 | 11/2014 | Bozarth |
| 8,880,406 B2 | 11/2014 | Santos-lang et al. |
| 8,924,211 B2 | 12/2014 | Ganong et al. |
| 8,953,886 B2 | 2/2015 | King et al. |
| 8,972,243 B1 | 3/2015 | Strom et al. |
| 8,977,555 B2 | 3/2015 | Torok et al. |
| 9,031,926 B2 | 5/2015 | Milward et al. |
| 9,058,805 B2 | 6/2015 | Aleksic et al. |
| 9,117,451 B2 | 8/2015 | Fructuoso et al. |
| 9,129,013 B2 | 9/2015 | Delaney et al. |
| 9,135,571 B2 | 9/2015 | Delaney et al. |
| 9,147,054 B1 | 9/2015 | Beal et al. |
| 9,152,763 B2 | 10/2015 | Carus et al. |
| 9,208,217 B2 | 12/2015 | Milward et al. |
| 9,240,187 B2 | 1/2016 | Torok et al. |
| 9,257,120 B1 | 2/2016 | Alvarez Guevara et al. |
| 9,269,012 B2 | 2/2016 | Fotland |
| 9,292,089 B1 | 3/2016 | Sadek |
| 9,304,736 B1 | 4/2016 | Whiteley et al. |
| 9,318,104 B1 | 4/2016 | Fructuoso et al. |
| 9,324,323 B1 | 4/2016 | Bikel et al. |
| 9,343,062 B2 | 5/2016 | Ganong et al. |
| 9,378,734 B2 | 6/2016 | Ganong et al. |
| 9,384,735 B2 | 7/2016 | White et al. |
| 9,424,840 B1 | 8/2016 | Tart et al. |
| 9,443,509 B2 | 9/2016 | Ganong et al. |
| 9,466,294 B1 | 10/2016 | Tunstall-pedoe et al. |
| 9,538,005 B1 | 1/2017 | Nguyen et al. |
| 9,542,944 B2 | 1/2017 | Jablokov et al. |
| 9,542,947 B2 | 1/2017 | Schuster et al. |
| 9,552,816 B2 | 1/2017 | Vanlund et al. |
| 9,563,955 B1 | 2/2017 | Kamarshi et al. |
| 9,569,594 B2 * | 2/2017 | Casella dos Santos ........................ G16Z 99/00 |
| 9,570,076 B2 | 2/2017 | Sierawski et al. |
| 9,601,115 B2 | 3/2017 | Chen et al. |
| 9,678,954 B1 | 6/2017 | Cuthbert et al. |
| 9,679,107 B2 | 6/2017 | Cardoza et al. |
| 9,721,570 B1 | 8/2017 | Beal et al. |
| 9,786,281 B1 | 10/2017 | Adams et al. |
| 9,792,914 B2 | 10/2017 | Alvarez Guevara et al. |
| 9,805,315 B1 | 10/2017 | Cohen et al. |
| 9,898,580 B2 | 2/2018 | Flanagan et al. |
| 9,904,768 B2 | 2/2018 | Yegnanarayanan |
| 9,911,418 B2 | 3/2018 | Chi |
| 9,916,420 B2 | 3/2018 | Cardoza et al. |
| 9,922,385 B2 | 3/2018 | Yegnanarayanan |
| 9,971,848 B2 | 5/2018 | D'souza et al. |
| 10,032,127 B2 | 7/2018 | Habboush et al. |
| 2006/0020466 A1 | 1/2006 | Cousineau et al. |
| 2009/0326937 A1 * | 12/2009 | Chitsaz .................. G10L 15/24 704/235 |
| 2011/0202370 A1 | 8/2011 | Green et al. |
| 2012/0278102 A1 | 11/2012 | Johnson |
| 2013/0110547 A1 | 5/2013 | Englund et al. |
| 2014/0019128 A1 * | 1/2014 | Riskin .................. G16H 10/60 704/235 |
| 2015/0340033 A1 | 11/2015 | Di Fabbrizio et al. |
| 2017/0329749 A1 | 11/2017 | Milward et al. |
| 2018/0012604 A1 | 1/2018 | Guevara et al. |
| 2018/0018966 A1 * | 1/2018 | Leonard ............. G16H 10/60 |
| 2018/0150605 A1 * | 5/2018 | Co ..................... G10L 15/063 |
| 2020/0350072 A1 * | 11/2020 | McEwing ............. G16H 50/70 |

* cited by examiner

FIG. 2A.

CARRIER 2:55 PM
MARSHALL, JIM   MRN: 1223456655522
37 YEARS MALE

REVIEW

CHIEF COMPLAINT

DOCUMENTS

ALL PHYSICIAN NOTES
LAST 4 DOCUMENTS

MAY 15, 2018 16:28
TEST SAME EXISTING CLINICAL NOTE
CONSULTATION NOTE
JUNIT, USER: SYSTEM, SYSTEM

APR 5, 2018 12:05
RTF WITH JPEG IMAGE
ADMISSION NOTE-PHYSICIAN
SYSTEM, SYSTEM

APR 5, 2018 12:01
RTF WITH EMBEDDED IMAGE
ADMISSION NOTE-NURSING
SYSTEM, SYSTEM

CARRIER 2:55 PM — 201
N/A THIS PATIENT RECEIVING ANY NARCOTIC?
37 YEARS MALE   MEDS 1223456655522 — 207

REVIEW — 202
ACETAMINOPHEN HYDROCODONE
(NORCO 325 mg-5 mg ORAL TABLET)
CHIEF COMP 325 mg/L, ORAL, DAILY

ASPIRIN-HYDROCODONE
DOCUMEN 2 amp, BUCCAL, 10X/DAY — 203

ALL PHYSICIAN NOTES
LAST 4 DOCUMEN MORPHINE — 204
20 mg, ORAL, Q4HR, PRN: PAIN

MAY 15, 2018 16:28
TEST SAME EXISTING CLINICAL NOTE
ACETAMINOPHEN HYDROCODONE (VICODIN)
1 TAB(S), ORAL, ONCE — 205

APR 5, 2018 12:05
RTF WITH JPEG IMAGE
ADMISSION NOTE-PHYSICIAN
SYSTEM, SYSTEM

APR 5, 2018 12:01
RTF WITH EMBEDDED IMAGE
ADMISSION NOTE-NURSING
SYSTEM, SYSTEM — 206

APR 5, 2018 12:01

SEMANTICALLY AUGMENTED CLINICAL SPEECH PROCESSING

CROSS REFERENCE TO RELATED APPLICATIONS

This application is a continuation of U.S. application Ser. No. 16/720,628, filed on Dec. 19, 2019 and entitled "Semantically Augmented Clinical Speech Processing," which claims the benefit of priority to U.S. Provisional Application No. 62/784,910, filed on Dec. 26, 2018, entitled "Semantically Augmented Clinical Speech Processing," the entireties of which are incorporated herein by reference.

BACKGROUND

Modern natural language processing (NLP) or understanding (NLU) tools are very powerful tools that allow systems to fairly accurately recognize the intent of text. Common goals of the available NLP or NLU tools are to be able to build applications that are so much more engaging and provide human-like conversation interactions. In order to build these highly engaging conversational applications, developers need to train these engines because they do not work for any particular application out of the box.

In a medical domain, the conversational, dictation, and command speech almost always contain a plethora of specific medical terms not present in typical conversation. These medical terms are described by standard and custom terminologies such as SNOMED CT®, LOINC®, etc. Existing methods of speech processing lack the clinical semantic meaning of these terms.

There are hundreds of thousands of these medical terms. In order for a given NLP or NLU engine to be effective in a medical domain, all of these terms must be properly loaded into these tools. The NLP models must be properly loaded in order to produce accurate intent recognition results. Manual addition of these terms is extremely difficult and time-consuming. It is also not very efficient as the terms manually loaded cannot be reused across different NLP models for different applications. It would be beneficial to manage terminology terms and their inter-relationships and associated verbal phrases outside of a given NLP/NLU engine and have the ability to bulk load any given engine with the medical terminology content along with the specific intents and sample utterances.

SUMMARY

Systems, methods and computer-readable media are provided for processing voice input(s) to identify intents and mapped standard terminologies. Using natural language processing or understanding, an intent of a voice input is identified. The intent is utilized to identify a standard terminology that maps to the intent. The standard terminology is utilized to identify information relevant to the standard terminology in a patient's electronic health record.

BRIEF DESCRIPTION OF THE DRAWINGS

The present invention is described in detail below with reference to the attached drawing figures, wherein:

FIGS. 2A and 2B depict aspects of an illustrative graphical user interface (GUI) providing information utilizing voice input;

DETAILED DESCRIPTION

Figure 1A:
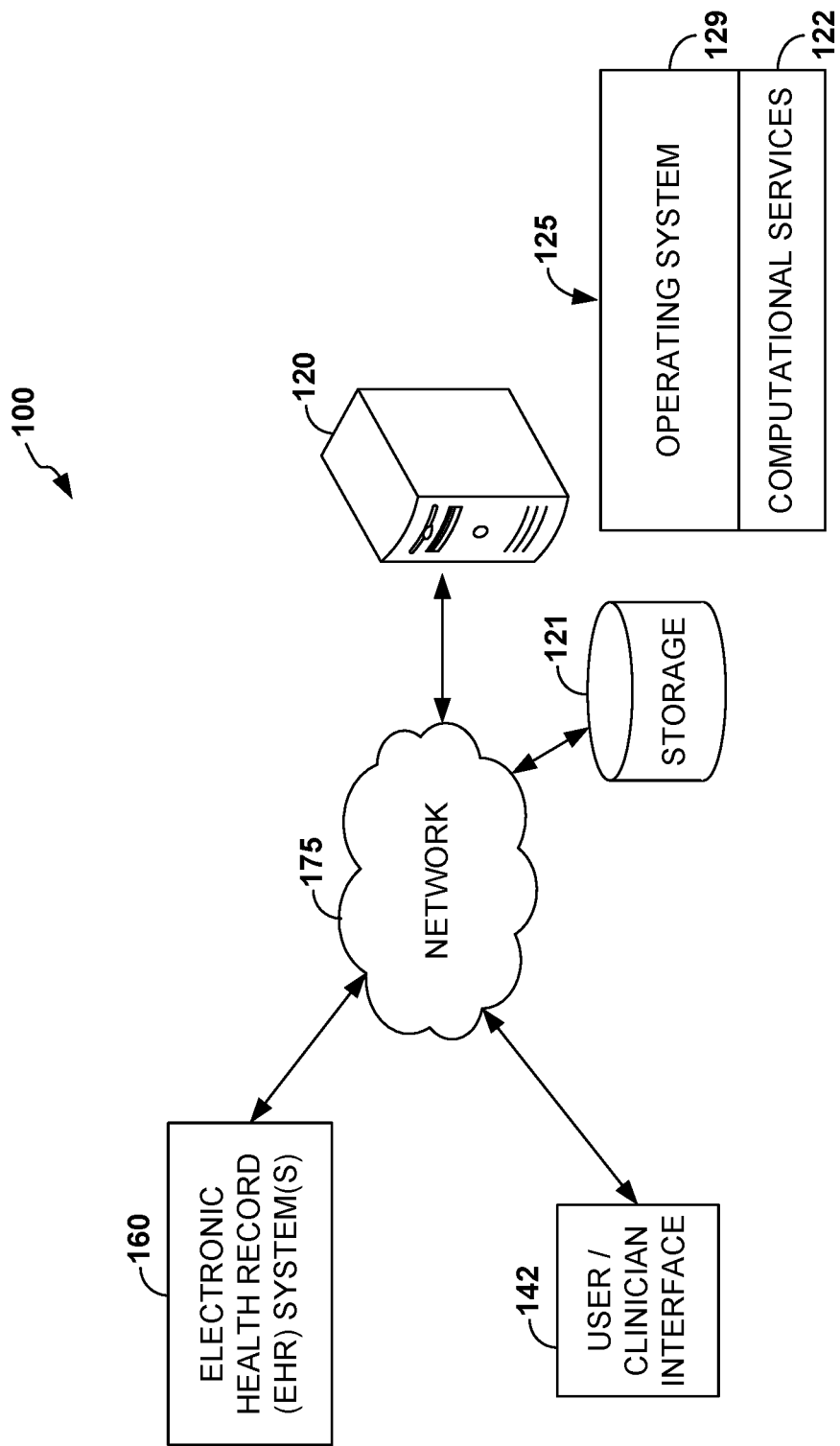
FIGS. 1A, 1B, and 1C depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media, as discussed further with respect to FIGS. 1A-1B.

Accordingly, at a high level, a speech processing and mapping service (SPMS) is provided that sits on top of system intelligence used to identify context and standard terminologies from voice input. The SPMS links at least an electronic health record (EHR) system, a NLP engine, a semantic mapper, a patient-specific information database, and a terminology graph together such that the SPMS coordinates processing of voice input.

The SPMS may coordinate a passive or active voice analysis system. A passive system, as used herein, refers to a voice system that is listening for voice input and translating that to a format that is consumable by a user, a system, or the like. In a passive system, the system is listening to a voice conversation or voice inputs and processing that information rather than taking an action or engaging with the user. An active system, as used herein, refers to a voice system that listens for voice input and takes action based on that input. In an active system, the user typically engages the system (e.g., the user may ask the system to do something or present something, etc.). Specific examples include translating a voice input to a documentation item (passive), translating a spoken order to a documentation-ready order item (passive), receiving a command to show a patient's last X-ray result and retrieving said result for presentation (active), collecting a patient history from a patient (active), prompting a user to take an action based on an input (active), and the like.

The system architecture described herein may be utilized with either a passive or an active system, or a combination thereof. The architecture described herein may be utilized to appropriately route inputs to the appropriate system. In other words, the architecture may route an input to a passive system, an active system, or both.

The SPMS is utilized to add intelligence to other system tools and connect the tools to a healthcare domain. The SPMS interfaces with, specifically, an EHR system. As used herein, the term "EHR" or "longitudinal EHR" refers to an electronic health record for an individual with documentation spanning across multiple encounters for the individual or at least one encounter prior to the current one for which the current electronic document is created. Accordingly, the documentation within the longitudinal EHR may be recorded at different times. The longitudinal EHR may also comprise at least some structured data. The data therein may be time and date stamped such that, in addition to providing the substance of those previous encounters, the longitudinal EHR provides a time line of the patient's care and, in some instances, one or more time series of physiological variables and clinical concepts related to the patient.

Accordingly, one aim of embodiments of this disclosure relates to applying the SPMS service to a NLP system and semantic mappers to process voice input(s). The voice input(s) comprise query requests, data entry requests, data collection interactions, commands to the system, and the like. The present disclosure seeks to extract information from a voice input(s), using NLP and a semantic mapper, and utilize information from the patient's electronic health record to validate the output, satisfy a request, prompt a next action, and the like.

Embodiments perform NLP on unstructured voice data to parse and extract intents, including entities and parameters of the entities. An entity, as used herein, refers to a classification of an intent. An intent may be associated with more than one entity. For instance, an order of "order atenolol 50 mg daily" results in an order entity with medication, dose, dose unit, and frequency being entities of the intent. Each entity is associated with one or more parameters identifying the entity. A parameter for "medication" in the present example would be "atenolol" while the parameter for "dose unit" is "mg."

Additional information may be parsed from the voice input including, but not limited to, a speaker, a role of the speaker, a time the voice input is spoken, etc. Additionally, the system can apply a temporal function such that concepts identified are classified as a past issue or a present issue (e.g., "I had some stomach pain but it seems better now. Headaches are still a concern" would result in a past stomach pain problem and a present headache problem).

The system further continues on by passing the intent (and the entities and parameters) to a semantic mapper to map the intent to a standard terminology. Standard terminologies include, but are not limited to, SNOMED CT®, LOINC®, etc. In embodiments, the standard terminology is a code value. The standard terminology is utilized to parse a patient data source to identify patient information corresponding to the standard terminology. The standard terminology is then appended to the intent to create a mapped intent response. The relevant patient data is then provided to a user via, in embodiments, a patient's EHR.

Today, well-formatted documents are the sources for NLP to identify clinical information during an encounter. These well-formatted documents make it very easy to identify clinical concepts, etc., because they are organized based on specific classifications. This cannot be said for voice data. The voice data is unstructured and subject to additional difficulties associated with conversations that do not apply to documents such as slang terminology, interruptions, unfinished sentences, dialects, speaking preferences or differences, inaudible inputs, etc.

Additionally, setting aside the difficulties of any voice input (inaudible inputs, interruptions, etc.), clinical voice input regarding clinical information is a completely different level of difficulty due to the vast clinical vocabulary associated therewith. Clinical terms are associated with a plethora of other clinical terms (that may mean the same thing to lay people) as well as numerous non-clinical terms used in everyday language that refer to the same thing. For instance, there are only a few ways to ask "what is the weather for today" and the response is predetermined but there are numerous ways to ask "how are you feeling today" and even more ways to respond to that question. Furthermore, "cold" may refer to a chill (i.e., temperature) or an upper respiratory infection, which also goes by many different names A patient reporting "a belly ache" is using a common term that may be associated with abdominal pain (or any number of other clinical conditions) but would not actually be found in any standard terminology, which leads to the next problem where even once a correct term is identified in a clinical conversation, it can then be associated with many different options. For example, "pneumonia" may trigger numerous coding options in ICD-10, as shown in the below table.

| | | |
|---|---|---|
| J18, Pneumonia, Unspecified Organism | | Non-Billable |
| J18.0 | Bronchopneumonia, unspecified organism | Billable |
| J18.1 | Lobar pneumonia, unspecified organism | Billable |
| J18.2 | Hypostatic pneumonia, unspecified organism | Billable |
| J18.8 | Other pneumonia, unspecified organism | Billable |
| J18.9 | Pneumonia, unspecified organism | Billable |

In addition to many different types of pneumonia triggered by the use of the word "pneumonia" there are several exceptions as well. For instance, there are special codes for aspiration pneumonia due to anesthesia during pregnancy (use Code 029), aspiration pneumonia due to solids and liquids (use Code J69), congenital pneumonia (use Code P23.0), and the like. The list goes on with various coding options for pneumonia.

Additionally, the medication "Atenolol" is associated with a specific code in a standard terminology while "Atenolol 50 mg" is associated with a different code. Furthermore, "Atenolol 50 mg daily" is associated with yet another code. This variance in standards for seemingly similar spoken terms is indicative of the vast vocabulary associated with clinical settings and clinical concepts.

Besides the expansive clinical vocabulary generally, many situations call for specific terms and will result in different concepts. For instance, a conversation in an oncology setting is going to be different than a conversation in a pathology setting. This is yet another example of the expansive clinical vocabulary that must be processed correctly to obtain accurate outputs.

Thus, conventional speech-to-text and NLP technologies are not capable of extracting accurate context from clinical voice conversations or inputs, at least, because they fail to integrate voice conversations, voice inputs, or voice commands with a patient's electronic health record (EHR). Additionally, current technologies fail to capture, recognize, and transcribe voice input into structured, usable data that may be incorporated into the patient's EHR or utilized to provide additional relevant information.

Referring now to the drawings in general and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural). Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

As shown in FIG. 1A, example operating environment 100 provides an aspect of a computerized system for compiling and/or running an embodiment for providing natural language processing or understanding of voice conversations. Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages, such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, the functions performed by these components, or the services carried out by these components may be implemented at appropriate abstraction layer(s), such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that, in some embodiments, functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems, and may be implemented in computer system 120. Similarly, EHR system 160 may perform functions for two or more of the EHR systems (not shown).

Continuing with FIG. 1A, network 175 may comprise the Internet, and/or one or more public networks, private networks, other communications networks, such as a cellular network or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items communicatively coupled to network 175 may be directly communicatively coupled to other items communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of the EHR system 160 include one or more data stores of health-related records, which may be stored on storage 121, and may further include one or more computers or servers that facilitate the storing and retrieval of the health records. In some embodiments, the EHR system 160 and/or other records systems may be implemented as a cloud-based platform or may be distributed across multiple physical locations. The EHR system 160 may further include record systems that store real-time or near real-time patient (or user) information, such as wearable sensor or monitor, bedside, or in-home patient monitors or sensors, for example. Although FIG. 1A depicts an example EHR system 160, it is contemplated that an embodiment relies on a speech processing and mapping service (SPMS), as further described herein, for storing and retrieving patient record information.

Example operating environment 100 further includes a user/clinician interface 142 communicatively coupled through network 175 to an EHR system 160. Although environment 100 depicts an indirect communicative coupling between interface 142 with EHR system 160 through network 175, it is contemplated that an embodiment of interface 142 may be communicatively coupled to EHR system 160 directly.

In some embodiments, interface 142 facilitates accessing and receiving information from a user or healthcare provider about a specific patient or set of patients, according to the embodiments presented herein. Embodiments of interface 142 also may facilitate accessing and receiving information from a user or healthcare provider about a specific patient, caregiver, or population including historical data; healthcare resource data; variables measurements; time series information; reference information, including clinical ontologies; and relational databases, as described herein; or other health-related information, and facilitates the display of results of the enhanced language process as described herein.

One embodiment of user/clinician interface 142 comprises a user interface that may be used to facilitate access by a user (including a healthcare provider or patient) to an assigned clinician, patient, or patient population. One embodiment of interface 142 takes the form of a graphical user interface and application, which may be embodied as a software application operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application, which may take the form of an applet or app, or a set of applications usable to manage user services provided by an embodiment of the technologies described herein.

Example operating environment 100 further includes computer system 120, which may take the form of one or more servers and which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations, such as one or more local clients and one or more remote servers, and may be distributed across the other components of example operating environment 100. For example, aspects of SPMS or user/clinician interface 142 may operate on or utilize computer system 120. Similarly, a portion of computing system 120 may be embodied on user/clinician interface 142, SPMS, and/or EHR system 160. In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as service 122. Some embodiments of operating system 129 comprise a distributed adaptive agent operating system. Embodiments of services may run as local services or may be distributed across one or more components of operating environment 100, in the cloud, on one or more personal computers or servers such as computer system 120, and/or a computing device running interface 142 or SPMS. In some embodiments, interface 142 and/or SPMS operate in conjunction with software stack 125.

Computational services 122 may perform statistical or computing operations such as computing functions or routines for processing of extracted information, as further described herein. Computational services 122 also may include natural language processing services (not shown) such as Discern nCode™ developed by Cerner Corporation, or similar services. In an embodiment, computational services 122 include the services or routines that may be embodied as one or more software agents or computer software routines. Computational services 122 also may include services or routines for utilizing one or more models, including logistic models. Some embodiments of the invention also may be used in conjunction with Cerner Millennium®, Cerner CareAware® (including CareAware iBus®), Cerner CareCompass®, or similar products and services.

In some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Example operating environment 100 also includes storage 121 (or data store 121), which in some embodiments includes patient data for a patient (or information for multiple patients), including raw and processed patient data; variables associated with patient diagnoses; and information pertaining to clinicians and staff, include user preferences. It is contemplated that the term "data" includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
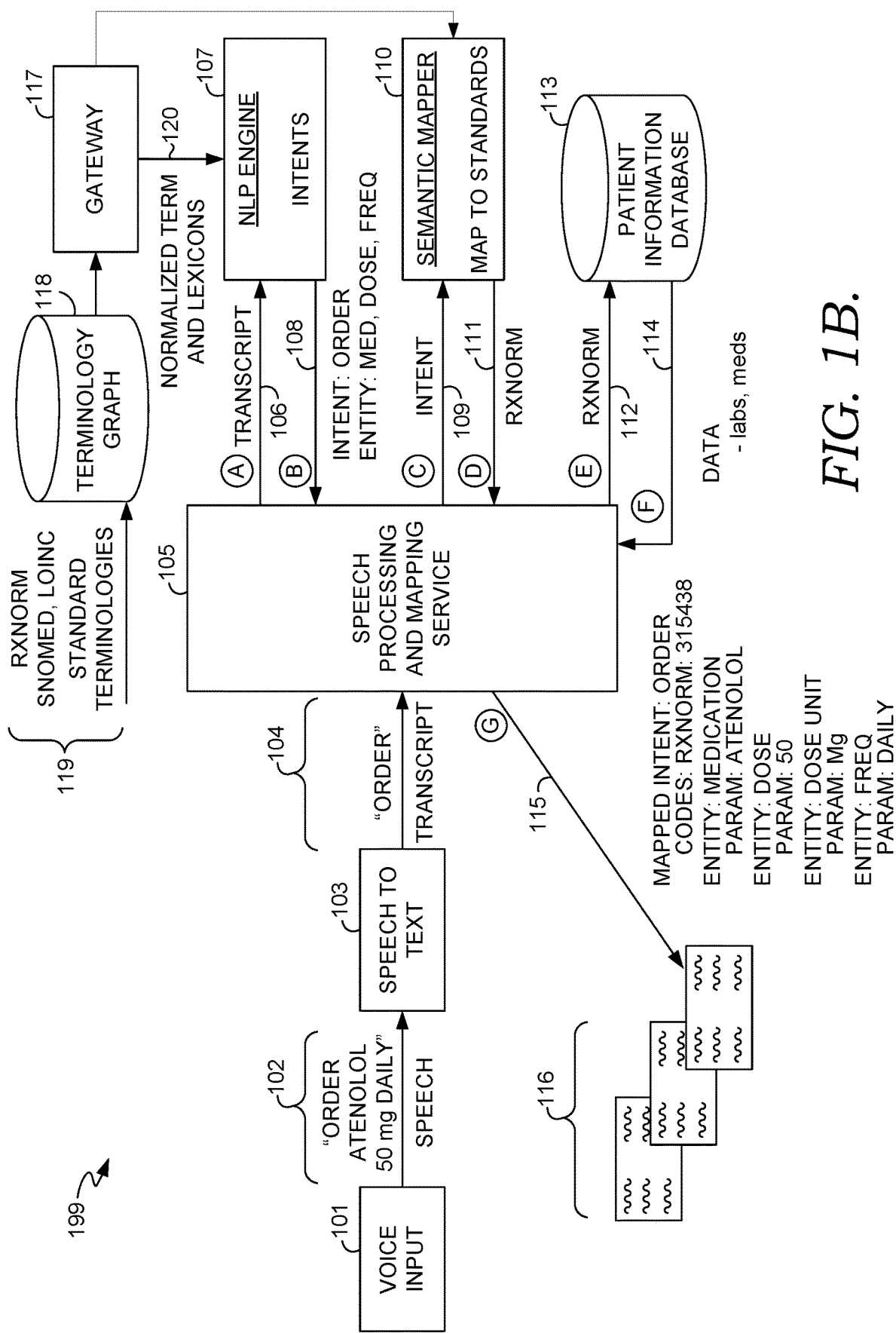

Turning now to FIG. 1B, an example computing architecture is provided that is suitable for use with embodiments of the present disclosure. The system comprises a speech to text service 103, the SPMS 105, a NLP application 107, a semantic mapper 110, a patient information database 113 (or patient data source), a terminology graph 118, and a gateway 117.

The terminology graph 118, as used herein, is an organizational graph comprising inter-relationships of a plurality of terms. The relationship generally includes at least a clinical term in each relationship. For instance, diabetes (a clinical condition) may be listed as related to medications that are used to treat diabetes. Additionally, the terminology graph 118 includes relationships of clinical terms to non-clinical terms. A clinical term, as used herein, refers generally to a term that is associated with a standard terminology (such as SNOMED, for instance). A non-clinical term, as used herein, refers generally to a term that is not associated with a standard terminology. As previously mentioned, "belly ache" is not associated with a standard terminology and is, thus, not a clinical term as used herein. It is, however, a non-clinical term that may be associated with a clinical term (or many clinical terms) in the terminology graph. Each term, clinical or non-clinical, may be associated with any number of other terms. The terminology graph 118 tracks those relationships for use by the system 199.

The terminology graph 118 includes one or more lexical variants that map to standard terminologies. A lexical variant, as used herein, refers generally to one or more different word forms for the same expressions. This differs from synonyms (which are also included in the terminology graph) in that synonyms are terms whose meanings are regarded as the same or nearly the same in a wide range of contexts (e.g., different terms for the same concept). For instance, exemplary synonyms include, but are not limited to, cats and felines, salt and sodium chloride, aspirin and acetylsalicylic acid, sweat and perspiration, etc. Exemplary lexical variants may include belly ache (for abdominal discomfort), cramps (for abdominal pain), bellyache, etc. Each variant or term is associated with at least one clinical term that maps to a standard terminology. For example, Atenolol (and all the related concepts to which Atenolol is associated) maps to one or more standard terminologies.

Example terms and standard terminology mappings are provided in the below table:

| CodeSysAbbr | Code | SNOMED-CT Full Name | Lexical Variant to Recognize |
| --- | --- | --- | --- |
| SNOMEDCT | 177250006 | Abdominoplasty (procedure) | Tummy tuck |
| SNOMEDCT | 21522001 | Abdominal pain (finding) | Belly pain |
| SNOMEDCT | 21522001 | Abdominal pain (finding) | bellyache |
| SNOMEDCT | 43364001 | Abdominal discomfort (finding) | Belly pain |
| SNOMEDCT | 43364001 | Abdominal discomfort (finding) | bellyache |
| SNOMEDCT | 9991008 | Abdominal colic (finding) | cramps |

The terminology graph 118 is referred to herein and, in an embodiment, is a graph. The relationships described herein do not have to be embodied in a terminology graph but could, instead, be tracked in any other known way to provide such relationships (e.g., an ontology).

Said relationships are key to providing accurate results from voice inputs, whether it is a documentation-type item, information requested by the voice input, action requested by the voice input, and the like. However, the relationships are not enough. The terminology graph 118 itself does not know, when the system 199 is asked if a patient is on a beta blocker, if the patient is, in fact, on a beta blocker. A connection between the terminology graph 118 and intelligence to respond to the input is required.

Gateway 117 provides such a connection. Gateway 117 communicatively connects the terminology graph 118 to the rest of system 199. In particular, the terminology graph 118 is accessible, via the gateway 117 to, for instance, the SPMS 105, the NLP engine 107, and the semantic mapper 110. The gateway 117 is configured to load speech content, phrases, relationships, etc., from the terminology graph 118 to any NLP application utilized, such as NLP engine 107. The NLP engine may be multiple NLP engines and may all be disparate. Custom content may be stored by the gateway 117 (or the terminology graph 118) for each NLP engine such that a customized set of data can be loaded to the appropriate engine.

In embodiments, the gateway 117 traverses the terminology graph 118 to identify content to load such as updated content, new content, etc. The gateway 117 can also filter out duplicate content and remove special characters for consumption by the NLP engine. In additional embodiments, the gateway 117 allows model input into, potentially, third-party solutions in bulk.

The system further comprises SPMS 105. The SPMS 105 is a service that can be utilized with any application (such as NLP engine 107, semantic mapper 110, and the like) and sits on top of/interacts with any intelligent tool (e.g., intent analysis, conversational bots, etc.). The SPMS 105 adds intelligence to the clinical information in embodiments. For instance, the SPMS 105 provides the connection between the intelligence that figures out what a voice input is intended to say (e.g., are you on a beta blocker) with the healthcare intelligence to identify the relevant information (e.g., beta blockers) so the SPMS 105 can identify the action needed and execute that action.

The system 199 further comprises NLP application 107. NLP application 107 may be configured to perform NLP or NLU on voice input(s) data. The NLP application 107 may be a third-party tool or not. The SPMS 105 is configured to operate with both third-party tools and tools that are within the same, for example, computing system. The NLP application 107 is utilized to identify an intent from a voice data input.

In an embodiment, NLP application 107 comprises a software application or set of applications (which may include programs, routines, functions, or computer-performed services) residing on a client computing device, such as a personal computer, laptop, smartphone, tablet, or mobile computing device or application 107 may reside on a remote server communicate coupled to a client computing device. As mentioned, in an embodiment, NLP application 107 is a Web-based application or applet and may be used to provide or manage user services provided by an embodiment of the technologies described herein, which may be used to provide, for example, semantic analysis on voice conversations.

A semantic mapper 110 is configured to map an intent to a standard terminology. As previously mentioned, the standard terminology may include SNOMED CT, LOINC, RxNORM, etc.

The SPMS 105 can then utilize the intent and the standard terminology to access relevant information from patient information database 113 (or patient data source). This information may be output to the user/clinician interface 116.

In application, the systems described herein apply various technologies (NLP, NLU, clinical ontologies, speech to text processing, etc.) to provide usable output for a user based on a voice input, as provided in FIG. 1B. Initially, a voice input is captured at block 101. A voice input may be an order (as shown by order 102), a request, a command, and the like. In embodiments, the voice input may be a passive input such as a parsed conversation or utterance from a conversation between, for example, a patient and a healthcare provider. In particular, the voice input(s) comprise query requests, data entry requests, data collection interactions, commands to the system, and the like. A query request, as used herein, refers generally to a question presented to the system for information. For instance, a user may ask "what is the patient taking for pain" or "what have they taken for pain in the last 24 hours?" These are questions to the system and a request to the system to provide information relevant to the request.

Data entry requests, as used herein, refer generally to a voice input that requests the system to input data. The data may be provided by the user or may be noted in a data source. For instance, a user may state "BP is 132/76,"

resulting in the system 199 placing the stated value in the patient's EHR. In embodiments, the system 199 may proactively provide additional information. By way of example, if the user stated "BP is 150/90," the system may identify this is a high blood pressure and take some action as a result (e.g., ask the user if they would like to prescribe X medication, etc.). This could be identified based on predetermined thresholds (e.g., values over a threshold are deemed high blood pressures), patient trends (e.g., a patient typically has a blood pressure below an identified average such that anything above that average may be deemed a high blood pressure for that patient), and the like.

Data collection interactions, a used herein, result in an active interaction between a user and the system 199. The system 199, in this instance, may collect information from the user (such as a history from a patient or clinician).

Commands to the system, as used herein, refer generally to a command to the system 199 to perform an action. Exemplary commands may include "navigate to order entry" in the user interface or "call a code" for a patient. Commands, via voice, result in the system 199 taking an ordered additional action. For example, a clinician may state "show me their shot record" to view a patient's shot record. The system may extract this information from a patient's EHR or any other records associated with the patient. The system may be integrated with the patient's EHR such that the portion of the record is directly shown or a link thereto may be provided.

Returning now to FIG. 1B, the voice input is illustrated as order 102 for "Atenolol 50 mg daily." The voice input is received by a speech to text component at block 103 and converted to a transcript of the voice input. The transcript may be generated in real-time or near real-time. In alternative embodiments, rather than a voice input being received at block 101, a user could manually begin typing inputs into the system and the process may begin at block 103.

Once transcribed, the voice input and unstructured transcript of the voice input, shown as numeral 104, is then routed to the SPMS 105 for an API call to a patient's record. Recall, the SPMS 105, in embodiments, is a service that sits on top of any intelligence and coordinates the communication of information between utilized tools.

The SPMS 105 calls the NLP engine 107 to identify an intent in the transcript, one or more entities associated with the intent, and one or more parameters of the one or more entities. The transcript, thus, is communicated to the NLP engine 107 at step 106. The NLP engine 107 identifies the intent of the voice input and communicates the intent back to the SPMS 105 at step 108. Intents can be identified from a plurality of intents loaded to the NLP engine 107. The plurality of intents can be configurable by a client and can be learned by the NLP engine 107 over time with the use of machine learning techniques.

In the present example, the intent is identified as follows:
Intent: Order
  Entity: Medication
    Param: Atenolol
  Entity: Dose
    Param: 50
  Entity: Dose Unit
    Param: mg
  Entity: Frequency
    Param: daily The NLP engine 107 has been loaded with information from the terminology graph 118 (via gateway 117). The NLP engine 107 uses this information to identify an entity or clinical concept (such as an order). For instance, in the query if the patient is on any beta blockers, the NLP engine 107 identifies the intent (e.g., that the user is asking whether the patient is on any beta blockers) and then utilizes the information from the terminology graph 118 to identify a list of beta blockers. This return of information is not possible if the terminology graph is not accessible or properly loaded into the NLP engine 107.

In addition, NLP engine 107 may also be utilized to identify context within the voice conversation. Context may be identified using a role of a speaker, a number of speakers, the specialty of the speaker, etc. For example, if a speaker is identified as an oncology clinician, a different context would apply than if the speaker were identified as, for example, a dermatologist. Furthermore, given the vast amount of information in clinical ontologies, once a particular context is identified (e.g., dermatologist rather than oncologist), only a context specific to that is provided rather than inundating the NLP engine 107 with non-relevant information. This can save on the processing power of the NLP engine 107 as it avoids needlessly parsing irrelevant data.

Once the intent is communicated back to the SPMS 105 at step 108, it is communicated to the semantic mapper 110 at step 109. The semantic mapper 110 maps the intents to standard terminologies to return a mapped standard terminology. For instance, when the NLP engine 107 identifies a list of beta blockers, the semantic mapper 110 identifies a standard terminology associated with each beta blocker on the list. In the present example where the user has ordered Atenolol, the semantic mapper 110 has mapped the medication to a RxNORM standard terminology and returns that at step 111 to the SPMS 105.

An accurate intent is crucial in order to properly map to the correct standard terminology. As previously mentioned, "Atenolol" maps to a different standard than "Atenolol 50 mg daily." The correct standards mapping is critical to an accurate output or result.

The SPMS 105 then executes a call for patient information. A FHIR call is an exemplary API call that may be utilized herein. The SPMS 105 communicates the standard terminologies to the patient information database 113 at step 112. The standard terminologies are necessary since FHIR, for instance, can only read standard terminologies. Furthermore, semantic mapper 110 can map to any number of standard terminologies, thus promoting interoperability with various sources using different standards.

The patient information database 113 may be any data store comprising patient information. Thus, it may be a part of EHR system 160 shown in FIG. A, a medication administration records database, and the like. The SPMS 105 utilizes the mapped standard terminology to identify information in the patient information database 113 that is relevant to or associated with the mapped standard terminology. For instance, in the present example, the order was mapped to an RxNORM standard. The SPMS 105 may then parse the patient information database 113 for any information including, or associated with, the RxNORM standard for Atenolol, 50 mg daily. This may include lab values, current medication lists, previous medication lists, pending prescriptions, and the like. The information is communicated back to the SPMS 105 at step 114.

In embodiments, standard terminologies may not be needed and an intent may suffice. For instance, if a clinician states "I reviewed your vitals, they look good," then the system may intelligently identify the clinical concept "vitals" and provide collected vital signs on a user interface. This information may be extracted from the patient's EHR. The information may also be identified from other devices, such as a heart monitor, etc., that may be associated with a patient. Integrated devices, while not shown in the figures, can be a source of information for the system 199.

The SPMS 105 can provide the information including the mapped intent, the entities and parameters associated with the intent, the mapped standard terminology, and/or the relevant patient-specific information to the user/clinician interface 116.

In some embodiments, the above described processing is automatically performed while a user, such as a clinician, is providing voice input. In other embodiments, an indication to start processing is received from an activate indication (e.g., "Hello, Scribe"). This can be useful in clinical settings where it is not desired that the system 199 would be constantly listening. Rather, an initiation cue can be utilized to initiate the processing described herein, in embodiments.

In embodiments, various outputs are provided to the user/clinician interface 116. For instance, various document formats may be generated from the voice input(s). One example document is structured and usable by the clinician with an aim to persist as part of the patient's record (e.g., doctor's notes, etc.). A second example document is transformed to a format consumable by the patient. The language and content may be tailored to the needs of the patient. A third example document may be tailored to the needs of referrals. For instance, if, during the voice conversation, a clinician recommends the patient meet with additional providers, a referral document may be generated.

In addition to documents, documentation items or action items may also be generated by the system. A documentation item or action item, as used herein, refers generally to data that would typically need to be documented in the patient's record either during or after the encounter. For example, a patient's vital signs or other clinical findings need to be documented in the patient's record during a visit. Additionally, any orders or prescriptions a clinician provides need to be documented in the patient's record. The present system automatically generates these documentation items. For instance, if a clinician says "I'm putting you on a Z-pack" the system intelligently knows that the clinician is placing an order ("putting you on" may be a cue that an order is to follow) for a medication. The prescription may be automatically generated by the system and populated on the user interface 116. From there, it may be automatically documented in the patient's record or it may be pending until signed or manually approved by the clinician. In additional embodiments, the system is linked to other programs such that it may be automatically communicated to an appropriate destination. For example, a medication prescription may be automatically sent to the pharmacy or an order for a chest X-ray may automatically be sent directly to radiology.

In additional embodiments, data other than voice may be captured during the encounter, such as movement, images, sensor data, videos, etc. This data may be captured and incorporated directly into the EHR and, thus, can be referenced during subsequent visits. For example, movement data (e.g., via sensors or a video) may be captured and used at a follow-up visit in three months to compare a gait, a facial identification can be used to identify a speaker, etc. Various in-room sensors may be used to capture data and include, but are not limited to, cameras, speakers, microphones, 3D cameras, wearable sensors, connected devices, and the like.

The architecture depicted in FIG. 1B is provided as one example of any number of suitable computer architectures, such as computing architectures that support local, distributed, or cloud-based software platforms, and are suitable for supporting computer system 120.

FIGS. 2A and 2B provide exemplary user interfaces provided by the system described herein. FIG. 2A is an exemplary view of a portion of a patient's EHR. This particular example is depicted on a mobile device but that is not necessary for the functions described herein. An indicator (such as the microphone in the top right corner of FIG. 2A) may be selected to initiate receiving of a voice input if not configured to automatically capture the voice input. A voice input in this example is "Is this patient receiving any narcotic meds?" The voice input, along with the results, is provided in FIG. 2B by way of an overlay (i.e., overlaying the patient record provided in FIG. 2A). As shown, the voice input 201 is provided ("is the patient receiving any narcotic meds"), along with a plurality of results 202, 203, 204, and 205 as an overlay to the view of the patient's EHR provided in FIG. 2A. This overlay allows a user to interact with the system via text, textual selection, voice, image, imagery selection, or any combination thereof. The overlay may provide access to secondary data such as whether a patient is on a particular type of medication.

A voice indicator 206 is provided to initiate additional voice capture, as well as the original voice indicator 201 from FIG. 2A. The overlay may be dismissed by selection of the exit indicator 207. Thus, the information output by the system described herein may be provided in combination with the patient's EHR as, for example, an overlay as provided in FIG. 2B, a split screen, or any other desired display format that provides the system output simultaneously with at least a portion of the patient's EHR. The overlay may further be configured such that hovering over (or any other configured selection/indication) a result may provide a link to an original source of the information. Additionally, while depicted as an overlay to a patient's EHR in this example, the overlay can be provided as an overlay to any application, even a third party application and is not limited solely to an EHR. For instance, a user could be in a message center and the voice overlay could be in the message center. Accessing this system in a message center might allow the user to query the EHR and then bring the EHR data to the user in the message center.

Figure 1C:
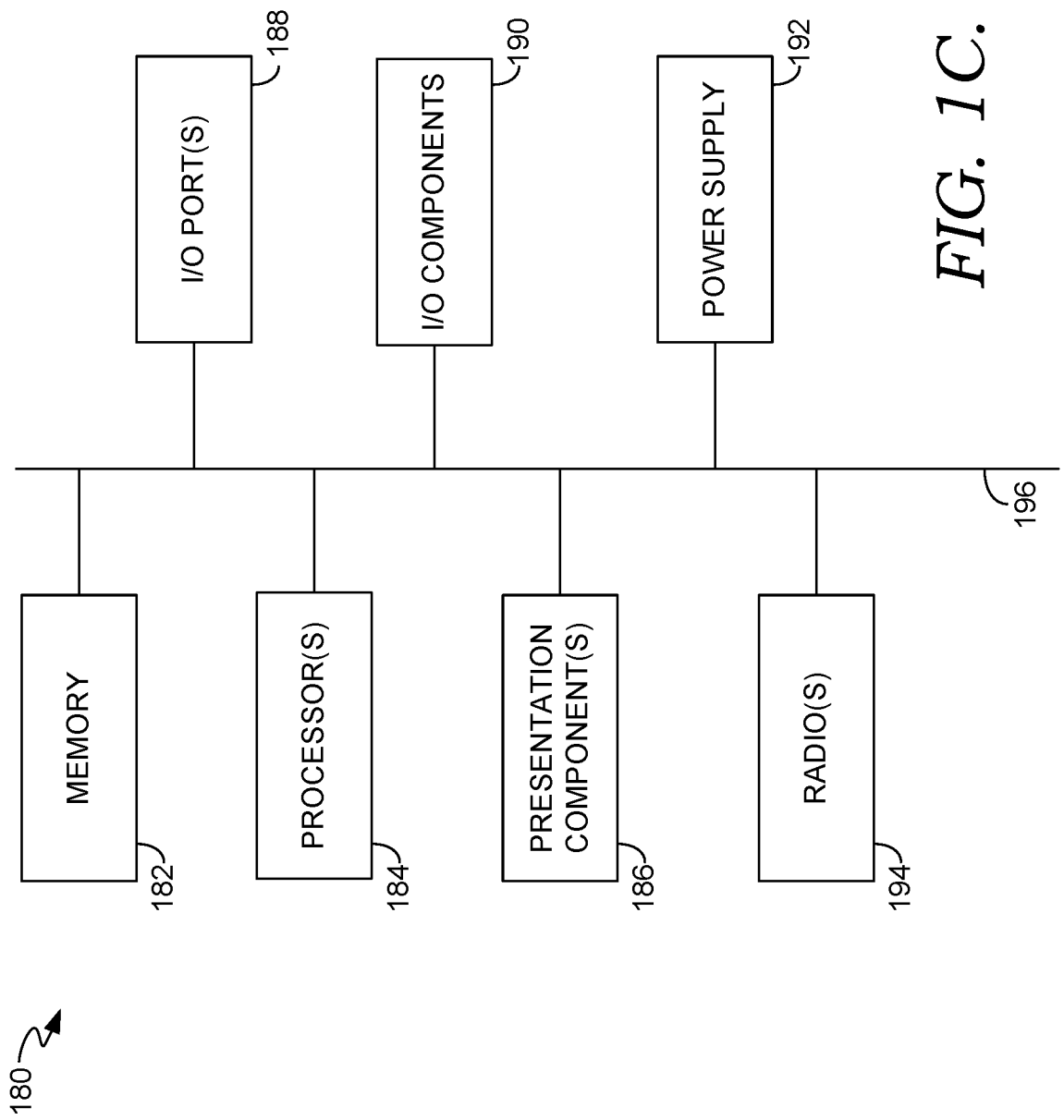

Turning now to FIG. 1C, there is shown one example embodiment of computing system 180 representative of a system architecture that is suitable for computer systems such as computer system 120. Computing device 180 includes a bus 196 that directly or indirectly couples the following devices: memory 182, one or more processors 184, one or more presentation components 186, input/output (I/O) ports 188, input/output components 190, radio 194, and an illustrative power supply 192. Bus 196 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1B and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 182 includes computer-storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 182 or I/O components 190. Presentation component(s) 186 present data indications to a user or other device. Exemplary presentation components include a display device, speaker, printing component, vibrating component, etc.

In some embodiments, computing system 194 comprises radio(s) 194 that facilitates communication with a wireless-telecommunications network. Illustrative wireless telecommunications technologies include CDMA, GPRS, TDMA, GSM, and the like. Radio 194 may additionally or alternatively facilitate other types of wireless communications including Wi-Fi, WiMAX, LTE, or other VoIP communications. As can be appreciated, in various embodiments, radio 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

Figure 3:
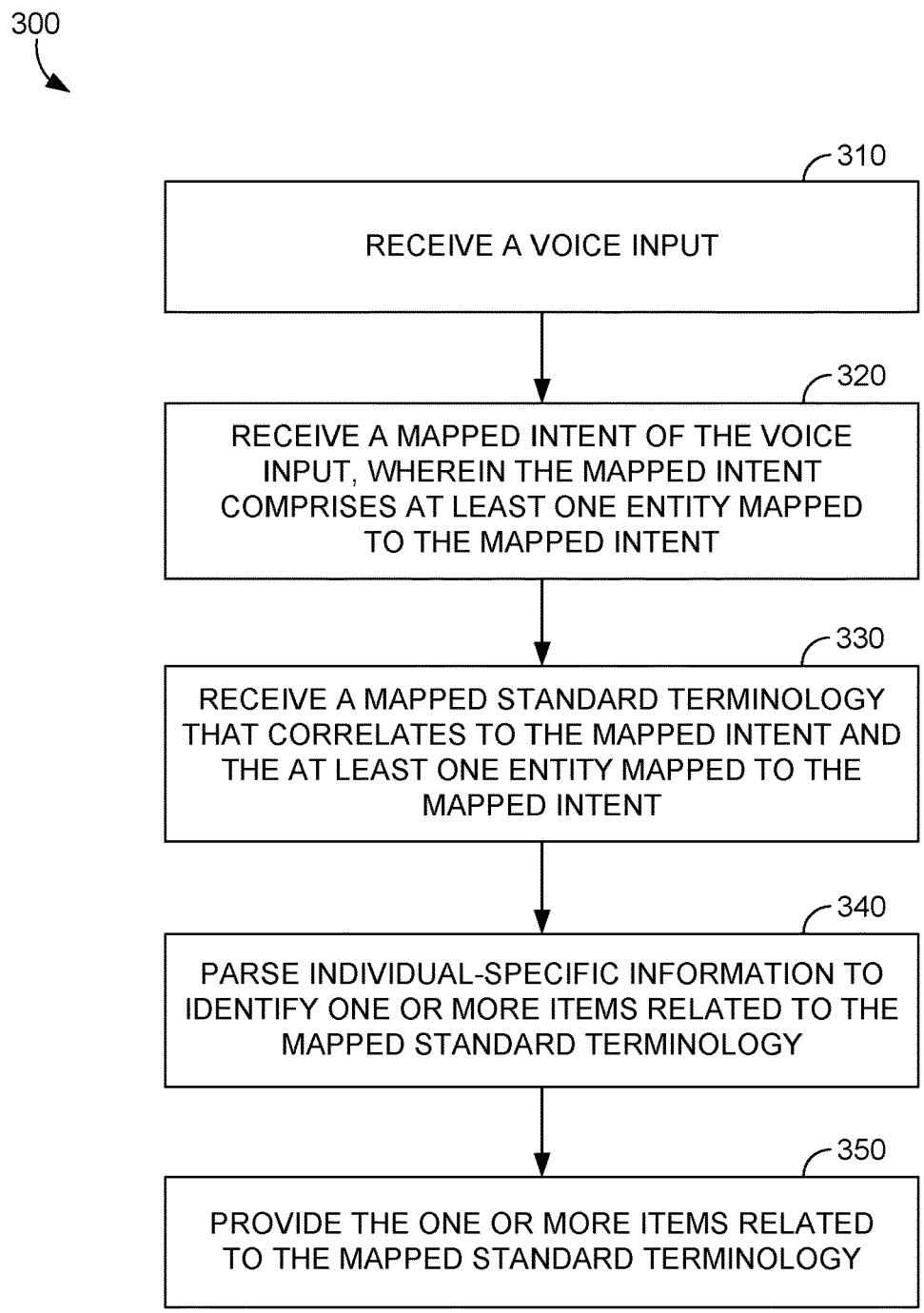
FIG. 3 depicts an exemplary method for processing voice inputs to identify intents and mapped standard terminologies in accordance with embodiments described herein.

Turning now to FIG. 3, an exemplary flow for a method 300 for processing voice inputs to identify intents and mapped standard terminologies is provided. Initially, at block 310, a voice input is received. The voice input is mapped to a mapped intent and received at block 320. The mapped intent comprises at least one entity mapped to the mapped intent. At block 330, a mapped standard terminology is received that correlates to the mapped intent and the at least one entity mapped to the mapped intent. Individual-specific information is parsed at block 340 to identify one or more items related to the standard terminology. At block 350, the one or more items related to the mapped standard terminology is provided.

Figure 4:
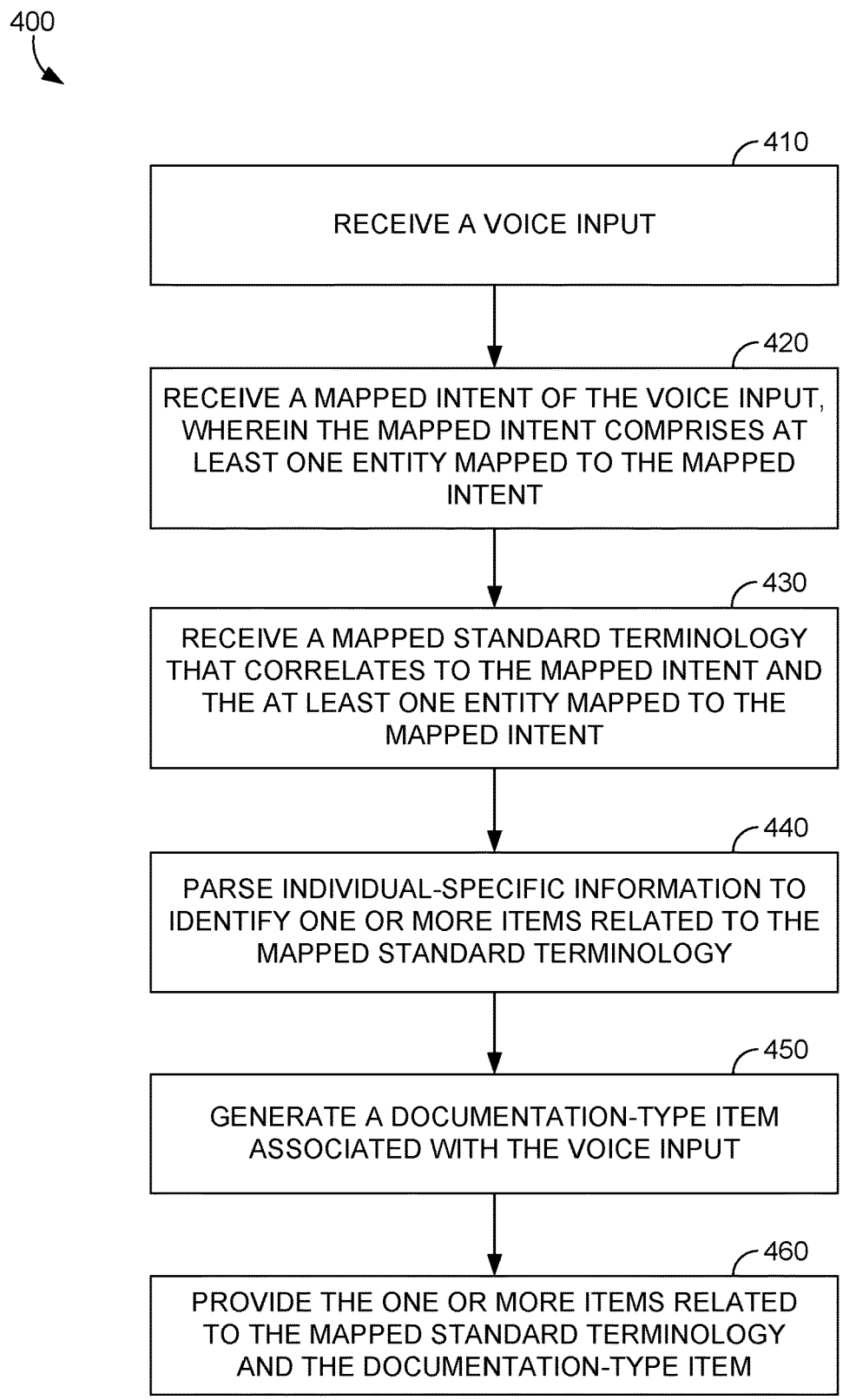
FIG. 4 depicts an exemplary method for processing voice inputs to identify intents and mapped standard terminologies in accordance with embodiments described herein.

FIG. 4 depicts an exemplary flow for a method 400 for processing voice inputs to identify intents and mapped standard terminologies is provided. Initially, at block 410 a voice input is received. The voice input is mapped to a mapped intent and received at block 420. The mapped intent comprises at least one entity mapped to the mapped intent. At block 430, a mapped standard terminology is received that correlates to the mapped intent and the at least one entity mapped to the mapped intent. At block 440, individual-specific information is parsed to identify one or more items related to the standard terminology. A documentation-type item associated with the voice input is generated at block 450. At block 460, the one or more items related to the mapped standard terminology and the documentation-type item are provided.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more non-transitory computer-readable media having computer-executable instructions embodied thereon that when executed by one or more processors, cause the one or more processors to perform a method, the media comprising, via the one or more processors:

obtaining a voice input that is associated with an individual;

transcribing by a voice analysis system and in real-time, the voice input that is associated with the individual;

extracting, from the transcribed voice input and by using a natural language processing engine that utilizes a terminology graph, an intent, wherein the terminology graph is an organizational graph comprising interrelationships of a plurality of terms, wherein the terms include clinical terms and non-clinical terms;

mapping the intent to a standard terminology by a semantic mapper using the terminology graph;

identifying data, by the voice analysis system and in real-time, in an electronic record specific to the individual that corresponds to the standard terminology; and causing a device to communicate, in a user-consumable format, the data identified that corresponds to the standard terminology identified and mapped to the intent.

2. The media of claim 1, further comprising performing natural language processing/understanding to the voice input.

3. The media of claim 1, wherein the voice input comprises one or more of a medical order, a data entry request, a query request, a data collection interaction, or a command.

4. The media of claim 3, further comprising:
electronically generating the medical order the corresponds to the voice input when the voice input comprises the medical order;
electronically entering and storing data values from the voice input when the voice input comprises the data entry request;
running a query that corresponds to the voice input and returning a search result when the voice input comprises the query request;
collecting data from the voice input when the voice input comprises the data collection interaction; or
performing a particular electronic function specified in the command when the voice input comprises the command.

5. The media of claim 1, further comprising identifying an entity associated with the intent identified.

6. The media of claim 5, further comprising identifying a parameter in the voice input, wherein the parameter is associated with the entity identified.

7. The media of claim 6, further comprising associating the entity and the parameter with the intent.

8. A computerized method comprising:
obtaining a voice input that is associated with an individual;
transcribing, by a voice analysis system and in real-time, the voice input that is associated with the individual;
identifying, by the voice analysis system and in real-time, an intent from the voice input transcribed and a standard terminology that maps to the intent;
extracting, from the transcribed voice input and by using a natural language processing engine that utilizes a terminology graph, an intent, wherein the terminology graph is an organizational graph comprising interrelationships of a plurality of terms, wherein the terms include clinical terms and non-clinical terms;
mapping the intent to a standard terminology by a semantic mapper using the terminology graph;
identifying data, by the voice analysis system and in real-time, in an electronic record specific to the individual that corresponds to the standard terminology; and
causing a device to communicate, in a user-consumable format, the data identified that corresponds to the standard terminology identified and mapped to the intent.

9. The computerized method of claim 8, further comprising performing natural language processing/understanding to the voice input.

10. The computerized method of claim 8, wherein the voice input comprises one or more of a medical order, a data entry request, a query request, a data collection interaction, or a command.

11. The computerized method of claim 10, further comprising:
electronically generating the medical order the corresponds to the voice input when the voice input comprises the medical order;
electronically entering and storing data values from the voice input when the voice input comprises the data entry request;
running a query that corresponds to the voice input and returning a search result when the voice input comprises the query request;
collecting data from the voice input when the voice input comprises the data collection interaction; or
performing a particular electronic function specified in the command when the voice input comprises the command.

12. The computerized method of claim 8, further comprising identifying an entity associated with the intent identified.

13. The computerized method of claim 12, further comprising identifying a parameter in the voice input, wherein the parameter is associated with the entity identified.

14. The computerized method of claim 13, further comprising associating the entity and the parameter with the intent.

15. A system comprising:
a computerized voice analysis system communicatively coupled to a microphone, the computerized voice analysis system having one or more processors that:
obtain a voice input that is associated with an individual via the microphone;
transcribe, in real-time, the voice input that is associated with the individual;
extract, from the transcribed voice input and by using a natural language processing engine that utilizes a terminology graph, an intent, wherein the terminology graph is an organizational graph comprising interrelationships of a plurality of terms, wherein the terms include clinical terms and non-clinical terms;
map the intent to a standard terminology by a semantic mapper using the terminology graph;
identify data, in real-time, in an electronic record specific to the individual that corresponds to the standard terminology; and
cause a device to communicate, in a user-consumable format, the data identified that corresponds to the standard terminology identified and mapped to the intent.

16. The system of claim 15, wherein the computerized voice analysis system further performs natural language processing/understanding to the voice input.

17. The system of claim 15, wherein the voice input comprises one or more of a medical order, a data entry request, a query request, a data collection interaction, or a command.

18. The system of claim 17, wherein the computerized voice analysis system further:
electronically generates the medical order the corresponds to the voice input when the voice input comprises the medical order;

electronically enters and storing data values from the voice input when the voice input comprises the data entry request;

runs a query that corresponds to the voice input and returning a search result when the voice input comprises the query request;

collects data from the voice input when the voice input comprises the data collection interaction; or performs a particular electronic function specified in the command when the voice input comprises the command.

19. The system of claim 15, wherein the computerized voice analysis system further identifies an entity associated with the intent identified.

20. The system of claim 19, wherein the computerized voice analysis system further:

identifies a parameter in the voice input, wherein the parameter is associated with the entity identified; and associates the entity and the parameter with the intent identified.

* * * * *